(12) United States Patent
Don Michael

(10) Patent No.: US 7,169,171 B2
(45) Date of Patent: Jan. 30, 2007

(54) DISTAL PROTECTION DOUBLE BALLOON CATHETER

(76) Inventor: T. Anthony Don Michael, 4109 Sill Pl., Bakersfield, CA (US)

(*) Notice: Subject to any disclaimer, the term of this patent is extended or adjusted under 35 U.S.C. 154(b) by 480 days.

(21) Appl. No.: 10/118,332

(22) Filed: Apr. 9, 2002

(65) Prior Publication Data

US 2003/0109916 A1    Jun. 12, 2003

Related U.S. Application Data

(63) Continuation-in-part of application No. 10/005,699, filed on Dec. 7, 2001.

(51) Int. Cl.
*A61F 2/06* (2006.01)

(52) U.S. Cl. .................................... 623/1.11

(58) Field of Classification Search ............... 623/1.11; 604/101.01–5, 103.05, 103.06; 606/194
See application file for complete search history.

(56) References Cited

U.S. PATENT DOCUMENTS

| | | | |
|---|---|---|---|
| 5,090,960 A | 2/1992 | Don Michael | |
| 5,135,484 A * | 8/1992 | Wright | 604/28 |
| 5,163,905 A | 11/1992 | Don Michael | |
| 5,195,955 A | 3/1993 | Don Michael | |
| 5,222,941 A | 6/1993 | Don Michael | |
| 5,306,249 A | 4/1994 | Don Michel | |
| 5,342,306 A | 8/1994 | Don Michael | |
| 5,380,284 A | 1/1995 | Don Michael | |
| 5,478,309 A | 12/1995 | Sweezer et al. | |
| 5,674,198 A * | 10/1997 | Leone | 604/101.05 |
| 5,728,068 A * | 3/1998 | Leone et al. | 604/101.01 |
| 5,971,955 A * | 10/1999 | Nap et al. | 604/101.05 |
| 6,165,196 A * | 12/2000 | Stack et al. | 606/194 |
| 6,267,747 B1 * | 7/2001 | Samson et al. | 604/103.07 |
| 6,364,900 B1 * | 4/2002 | Heuser | 623/1.11 |
| 6,485,500 B1 | 11/2002 | Kokish et al. | |

* cited by examiner

*Primary Examiner*—(Jackie) Tan-Uyen T. Ho
(74) *Attorney, Agent, or Firm*—Browdy and Neimark, PLLC

(57) ABSTRACT

A system for performing a medical treatment in a blood vessel while providing downstream microcirculatory system protection, the system being composed of: a catheter having a longitudinal axis, a distal end, an outer lateral surface, a central blood bypass flow lumen extending along the longitudinal axis and opening at the distal end, blood flow inlet and outlet openings extending from the lateral surface and communicating with the bypass flow lumen, and first and second inflation lumens extending to the lateral surface at respective first and second locations that are spaced apart along the longitudinal axis and that are between the inlet openings and the outlet openings; and first and second inflatable members secured to the lateral surface and each having an interior that communicates with a respective one of the first and second inflation lumens, wherein the catheter has a thin outer wall enclosing a hollow interior that is completely occupied by the bypass flow lumen, except for the space occupied by the first and second inflation lumens.

17 Claims, 8 Drawing Sheets

DISTAL PROTECTION DOUBLE BALLOON CATHETER

This is a continuation-in-part of U.S. application Ser. No. 10/005,699, filed on Dec. 7, 2001

BACKGROUND OF THE INVENTION

The present invention relates to the treatment of obstructions in body passages, and particularly in arteries.

Treatments of this type typically produce debris that, if allowed to enter the microcirculatory system downstream of the treatment site, can cause damage to organs and tissues.

BRIEF SUMMARY OF THE INVENTION

The invention provides a novel system that allows an angioplasty treatment, possibly with stenting or primary stenting, to be performed, while preventing the entry of debris resulting from such treatment into the distal microcirculatory system of a patient and assuring a continued supply of blood flow downstream of the obstruction during the angioplasty treatment and protection of organs and tissue downstream of the treatment site against damage that might be caused by debris resulting from the treatment.

The system according to the invention, for performing a medical treatment in blood vessels, is basically composed of: a catheter having a longitudinal axis, a distal end, an outer lateral surface, a central blood bypass flow lumen extending along the longitudinal axis and opening at the distal end, blood flow inlet and outlet openings extending from the lateral surface and communicating with the bypass flow lumen, and first and second inflation lumens extending to the lateral surface at respective first and second locations that are spaced apart along the longitudinal axis and that are between the inlet openings and the outlet openings; and first and second inflatable members secured to the lateral surface and each having an interior that communicates with a respective one of the first and second inflation lumens, wherein the catheter has a thin outer wall enclosing a hollow interior that is completely occupied by the bypass flow lumen, except for the space occupied by the first and second inflation lumens.

The annular bypass lumen is formed adjacent the outer wall of the catheter. Therefore, the blood inlet and outlet openings in communication with the bypass flow lumen can be formed in a simple manner. In addition, these openings can be made relative large to assure an adequate blood flow, a flow of at least 30 cc/min being considered necessary to maintain tissue viability.

BRIEF DESCRIPTION OF THE DRAWING

FIG. 5' is a view similar to, and in the same plane as, FIG. 5, showing a modified form of construction of the second embodiment.

DETAILED DESCRIPTION OF THE INVENTION

Figure 1:
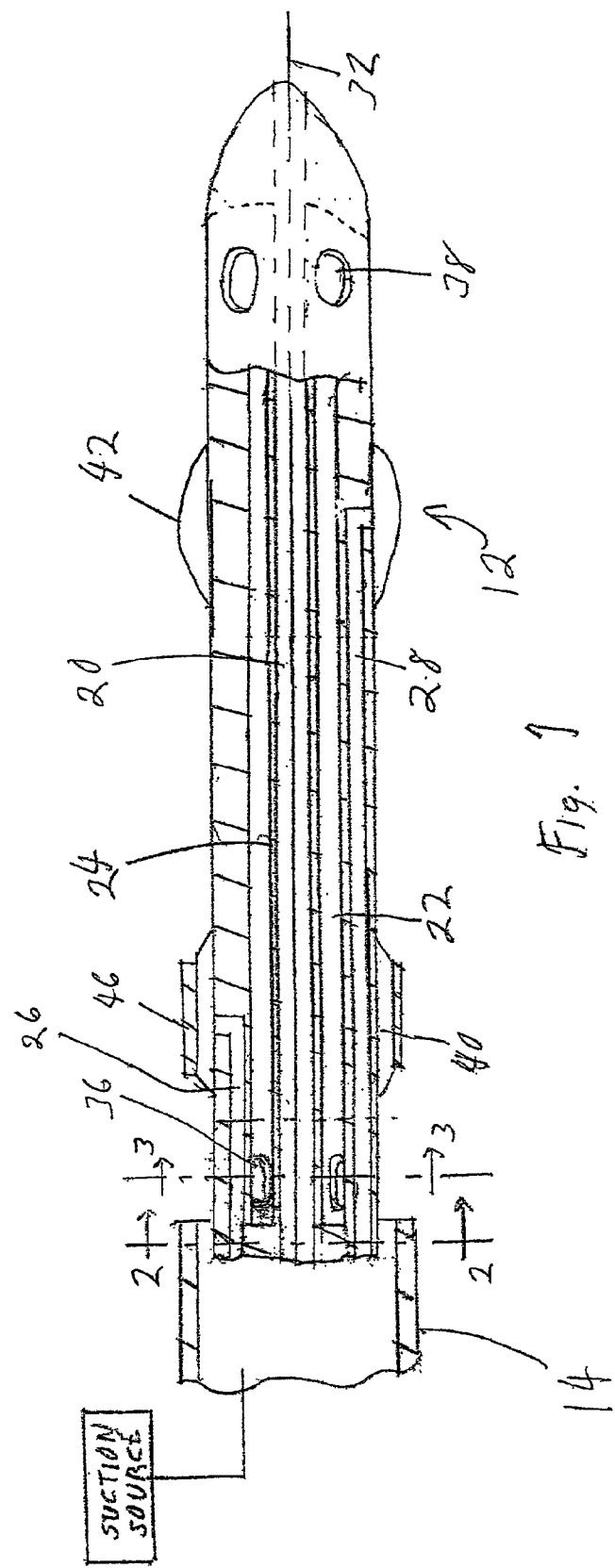
FIG. 1 is a side elevational view, partly in cross section, of one preferred embodiment of a catheter system according to the invention.

The following detailed description will be provided with reference to all three Figures.

The system according to the invention is composed essentially of a dilatation and embolic blocking catheter 12 and a surrounding, movable suction catheter 14, which may be in the form of a hypo tube.

Catheter 12 is provided with a central guidewire lumen 20 that is preferably coaxial with the longitudinal axis of catheter 12, a blood bypass flow lumen 22 that surrounds lumen 20 and is separated therefrom by a cylindrical wall 24, a proximal inflation lumen 26 and a distal inflation 28.

Lumen 20 extends the full length of catheter 12 and in open at the distal end thereof, which is the right-hand end in FIG. 1. Lumen 20 is provided to receive a guidewire 32 that serves to guide catheter 12 to a desired treatment site.

Catheter 12 is provided with a plurality of blood flow inlet openings 36 and a plurality of blood flow outlet openings 38, each set of openings 36, 38 being distributed circumferentially around the outer lateral wall of catheter 12. Openings 36 and 38 extend through the lateral wall of catheter 12 into communication with lumen 22. Lumen 22 does not extend through the full length of catheter 12. The proximal end of lumen 22 extends to a point upstream of openings 36, while the distal end of lumen 22 extends downstream of openings 38. According to the present invention, all openings 36, 38 communicating with lumen 22 extend through the lateral wall of catheter 12.

Catheter 12 is completed by two inflatable members 40 and 42 carried on the outer wall of catheter 12 and each communicating with a respective one of inflation lumens 26 and 28. According to preferred embodiments of the invention, member 40 is a low compliance angioplasty balloon, or sleeve, or sheath, and member 42 is a high compliance blocking balloon. Balloons 40 and 42 are located between openings 36, 38. It is particularly important that the blood flow path defined by lumen 22 extend across balloon 42 because that balloon remains inflated for a longer period of time, of the order of several minutes, than does balloon 40, of the order of a few seconds. In further accordance with the invention, balloon 40 carries a stent 46 that is to be expanded and deployed against the inner wall of a body passage to be treated.

Catheter 12 can also be provided with circular radiopaque bands adjacent to the proximal and distal edges of both balloons to assist in proper positioning of the catheter.

In practical embodiments of the invention, catheter 12 can have a size of 2–3 Fr (Fr is a notation indicating outside diameter; n Fr=n/3 mm), with a tapered tip, as shown, that helps to allow the catheter to traverse large obstructions.

The above-described device is manipulated to perform an angioplasty treatment in the following manner. Firstly, guidewire 32 is introduced into the blood vessel past the site where a treatment is to be performed. This can be achieved by any conventional procedure that allows guidewire 32 to be advanced through the vessel in the direction of blood flow, i.e. so that the distal end of guidewire 32 points downstream. After the guidewire has been advanced to a point beyond the location of the obstruction to be treated, for example with the aid of radiographic fluoroscopic monitoring, catheter 12 is placed over the guidewire so that the guidewire extends through lumen 20. Catheter 12 is then advanced over the guidewire to the site where the treatment is to be performed, specifically by bringing balloon 40 and stent 46, if provided, to a location opposite the obstruction.

Then, tube 14 is inserted in the blood vessel around catheter 12 and brought to a location substantially as shown in FIG. 1, upstream of the treatment site.

Then, balloon 42 is expanded by supplying a fluid at a suitable pressure, usually less than 1 atm, via lumen 28 to block the flow of blood between the outer wall of catheter 12 and the blood vessel wall. After balloon 42 has been thus inflated, blood continues to be supplied to the portion of the blood vessel downstream of catheter 12 by flowing through openings 36, lumen 22 and openings 38.

After balloon 42 has been inflated, balloon 40 is inflated by supplying a fluid at a suitable pressure via lumen 26 to press the obstruction outwardly and to expand and deploy stent 46. This operation generally results in the creation of debris consisting of material that has broken off from the obstruction. This debris will be prevented from flowing downstream of catheter 12 by inflated balloon 42 and will be trapped against the upstream side of balloon 42.

As soon as balloon 40 has been deflated, tube 14 is advanced in the downstream direction toward balloon 42 while suction is applied from an external suction source through tube 14. During this suctioning step, tube 14 can be moved back and forth along the axis of catheter 12 to aid the removal of debris. As a result, debris that has been trapped upstream of balloon 42 will be drawn into tube 14 and removed from the patient's body, where it can be inspected, possibly with the aid of a microscope. After suction has been performed for a sufficient time to assure removal of all debris, or at least all potentially dangerous debris, balloon 42 is deflated and tube 14 and catheter 12 are removed from the blood vessel.

Figure 3:
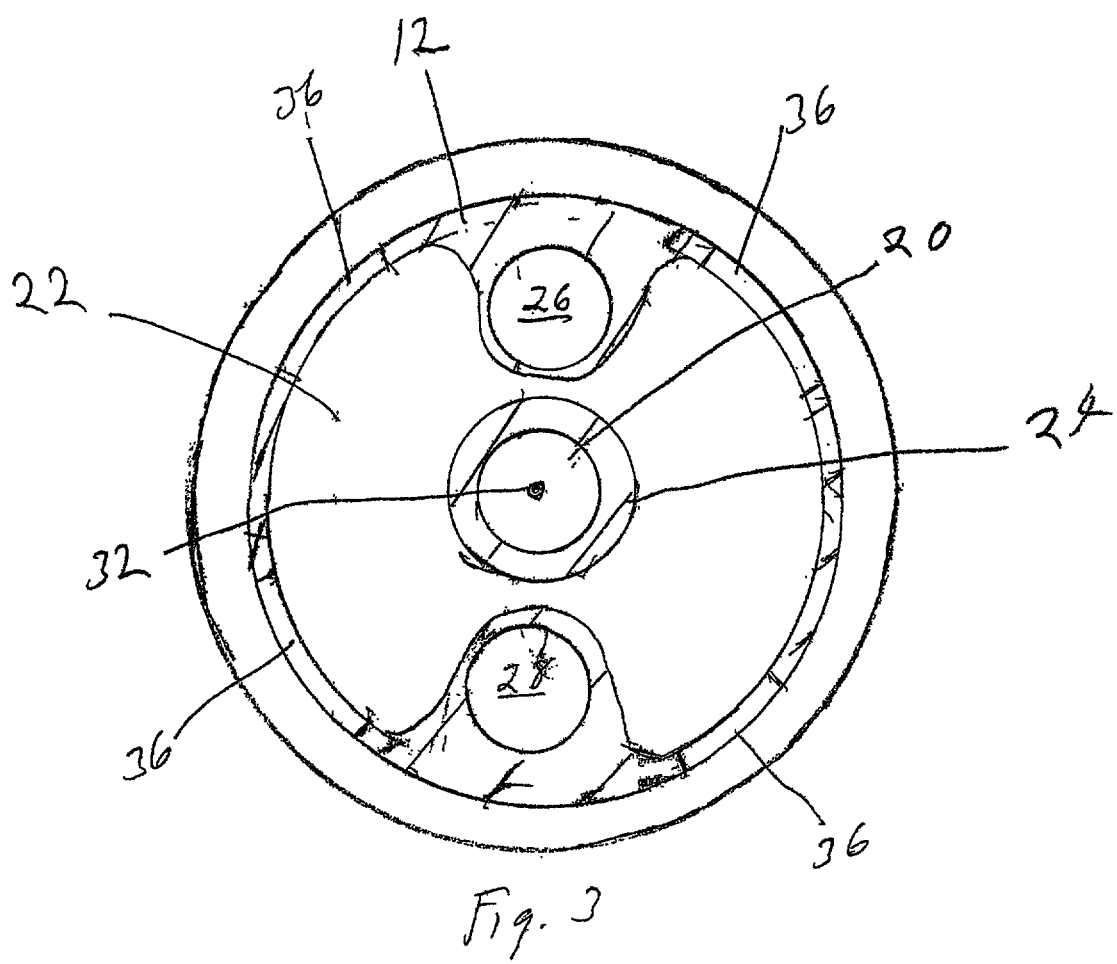
Figure 4:
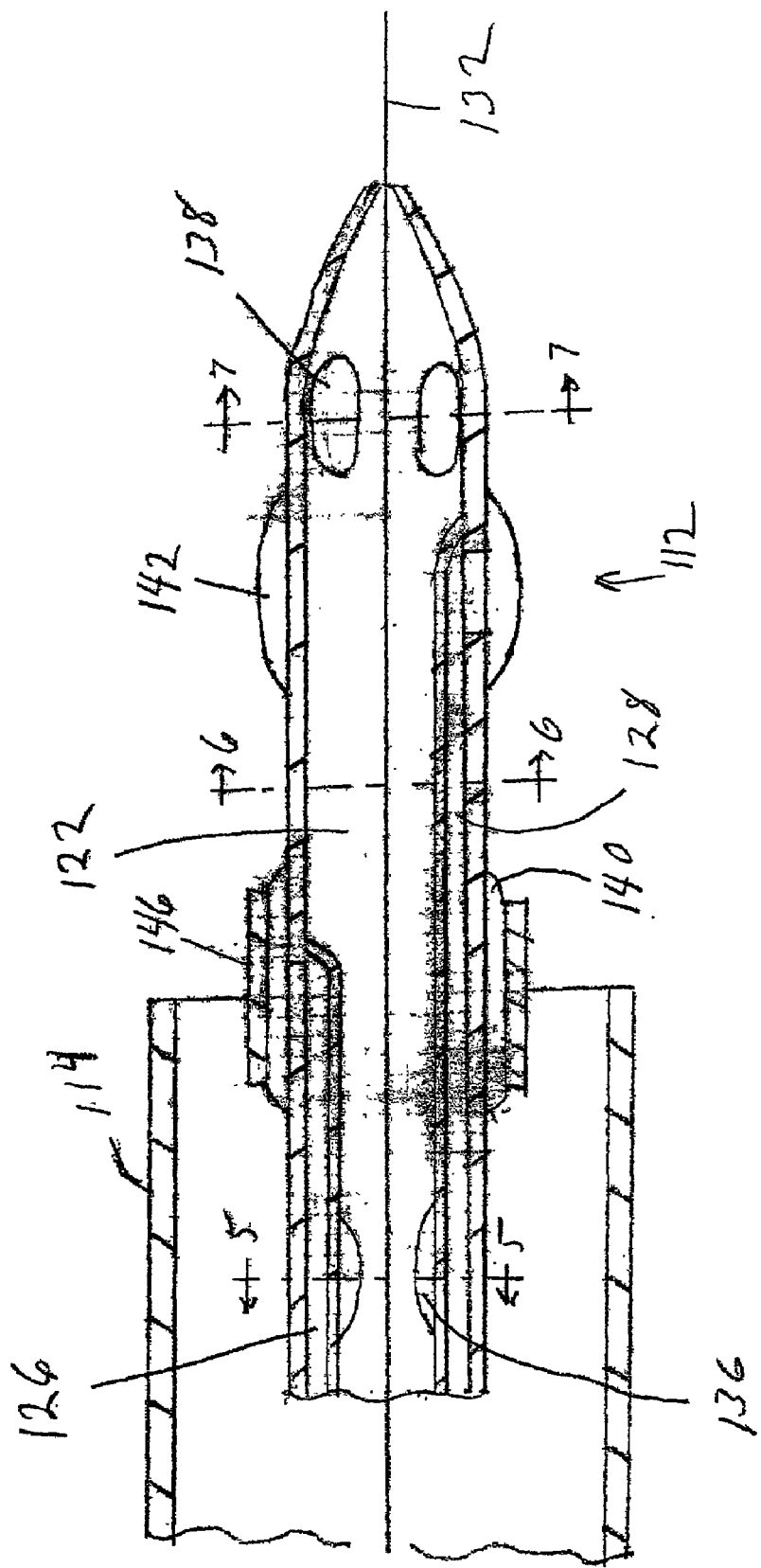
FIG. 4 is a view similar to that of FIG. 1 showing a second embodiment of the invention.
Figure 7:
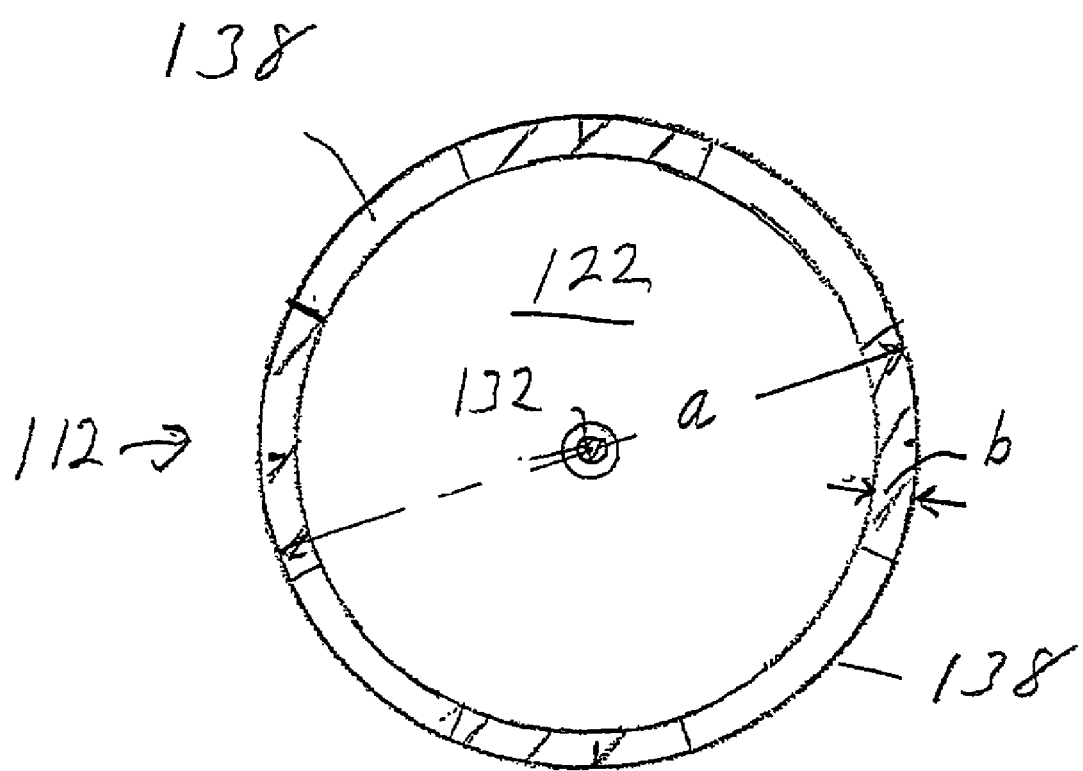

A second embodiment of the a system according to the invention is shown in FIGS. 4–3 7 and is composed essentially of a dilatation and embolic blocking catheter 112 and a surrounding, movable suction catheter 114, which may be in the form of a hypo tube.

According to this embodiment, catheter 112 is a thin-walled body that is hollow, except for balloon inflation lumens, to be described below, to provide a blood bypass flow lumen 122 having a maximum cross section. Catheter 112 is provided with a proximal balloon inflation lumen 126 and a distal balloon inflation 128. Lumens 126 and 128 are the only structures within catheter 112 and thus the only structures that reduce the cross section of lumen 122. Lumen 122 can, but need not, extend the full length of catheter 112 and has a small diameter opening at the distal end thereof for passage of a guidewire 132 that serves to guide catheter 112 to a desired treatment site. Preferably, the opening is made only slightly larger in diameter than guidewire 132 to allow more accurate guidance of catheter 112. If lumen 122 does not extend through the full length of catheter 112, the proximal end of lumen 22 may be located at a point upstream of openings 136, while the distal end of lumen 22 may be located downstream of openings 38, in the same manner as lumen 22 of FIGS. 1–3, while a guidewire lumen will be provided both proximally and distally of lumen 122.

Catheter 112 is provided with a plurality of blood flow inlet openings 136 and a plurality of blood flow outlet openings 138, each set of openings 136, 138 being distributed circumferentially around the outer lateral wall of catheter 112. All openings 136 and 138 extend through the lateral wall of catheter 112 into communication with lumen 122. A balloon or stent deployment sleeve or sheath 140 and a balloon 142 are carried on the outer surface of catheter 112 at locations between openings 136 and 138. It is particularly important that the blood flow path defined by lumen 122 extend across balloon 142 because that balloon remains inflated for a longer period of time, of the order of several minutes, than does balloon 140, of the order of a few seconds.

Balloon or sleeve 140 communicates via openings in the wall of catheter 112 with inflation lumen 126 and balloon 142 communicates via other openings in the wall of catheter 112 with inflation lumen 128. According to preferred embodiments of the invention, balloon 140 is a low compliance angioplasty balloon, sheath, or sleeve, and balloon 142 is a high compliance blocking balloon. In further accordance with the invention, balloon 140 carries a stent 146 that is to be expanded and deployed against the inner wall of a body passage to be treated.

Catheter 112 can also be provided with circular radiopaque bands adjacent to the proximal and distal edges of both balloons to assist in proper positioning of the catheter.

In practical embodiments of the invention, catheter 112 can have the following dimensions, identified in FIG. 7:
(a)—an outer diameter of 1.0 mm (3 Fr.);
(b)—a wall thickness of 0.127 mm.

However, the diameter of the catheter can have other values, for example between about 2 Fr and 5 Fr. According to another feature of the invention, dimension b can vary along the length of the catheter and can, for example have a greater value in a region aligned with balloon 140 than in a region between balloon 140 and the distal end of the catheter. A greater thickness in the region aligned with balloon 140 will help to keep the catheter from being compresses radially by the forces generated by balloon 140 during artery wall dilation, while a lesser thickness in the region between balloon 140 and the distal end of the catheter will give lumen 122 a larger cross section.

The provision of a tapered distal end, as shown, helps to allow the catheter to traverse large obstructions.

Figure 5:
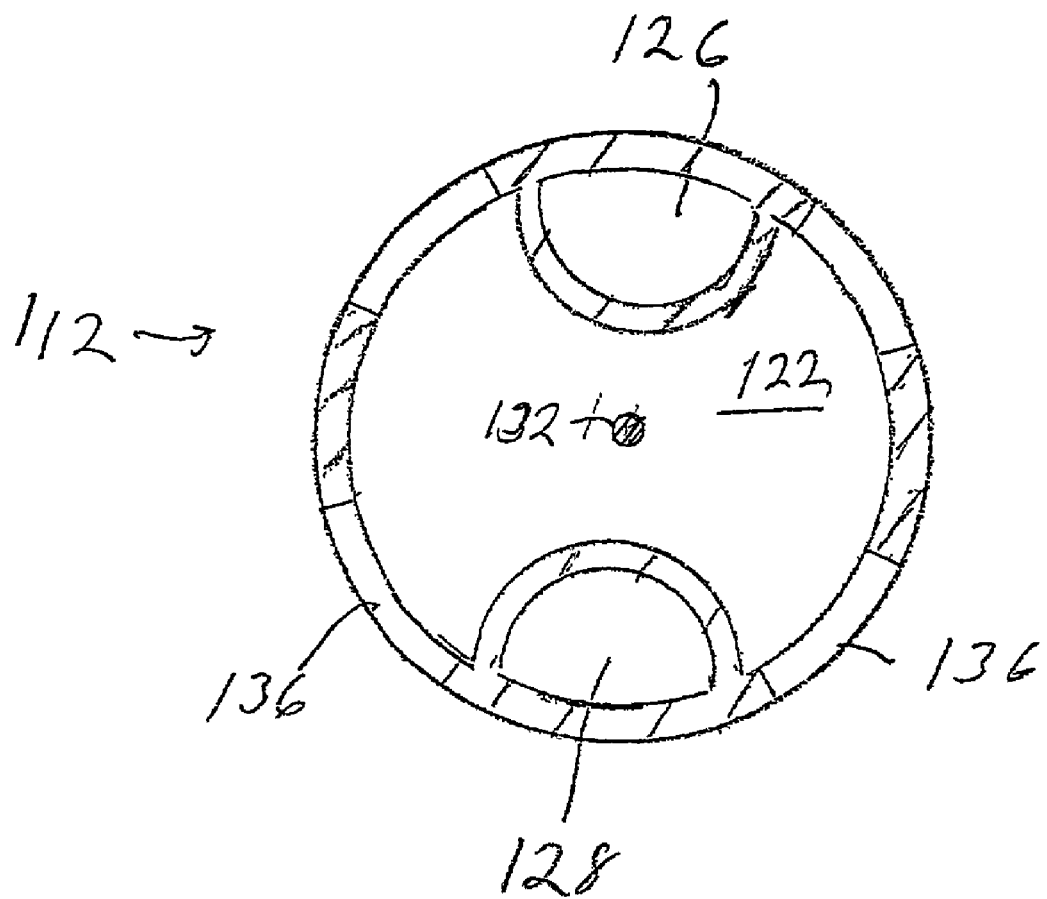
FIGS. 5, 6 and 7 are cross-sectional views taken along lines 5—5, 6—6 and 7—7, respectively, of FIG. 1.
Figure 6:
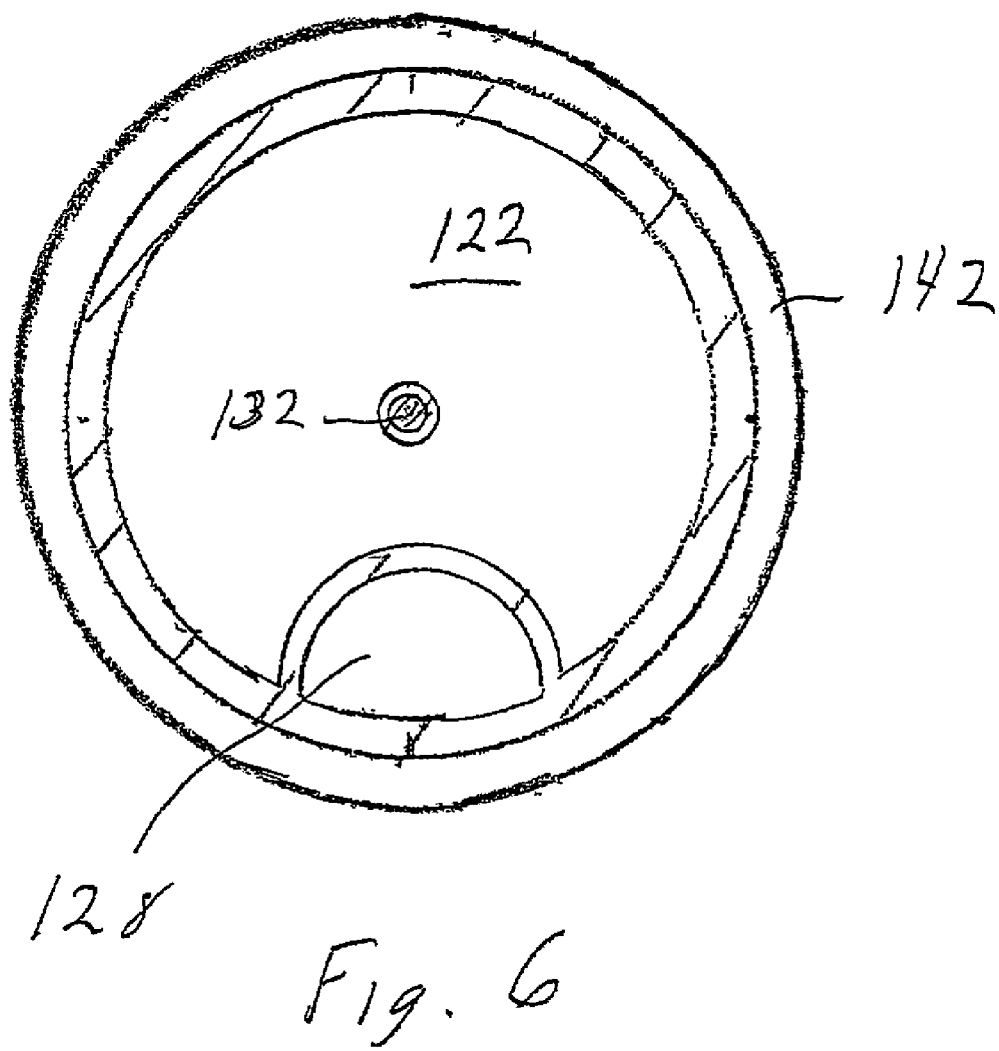

A modified version of the second embodiment is shown in FIG. 5'. This version differs from the embodiment of FIGS. 5–7 only in that one inflation lumen, such as, for example, lumen 128 of FIGS. 4–7, is replaced by a lumen 128' that extends outwardly from the outer lateral wall of catheter 112. This serves to enlarge the flow path provided by lumen 122.

Figure 8:
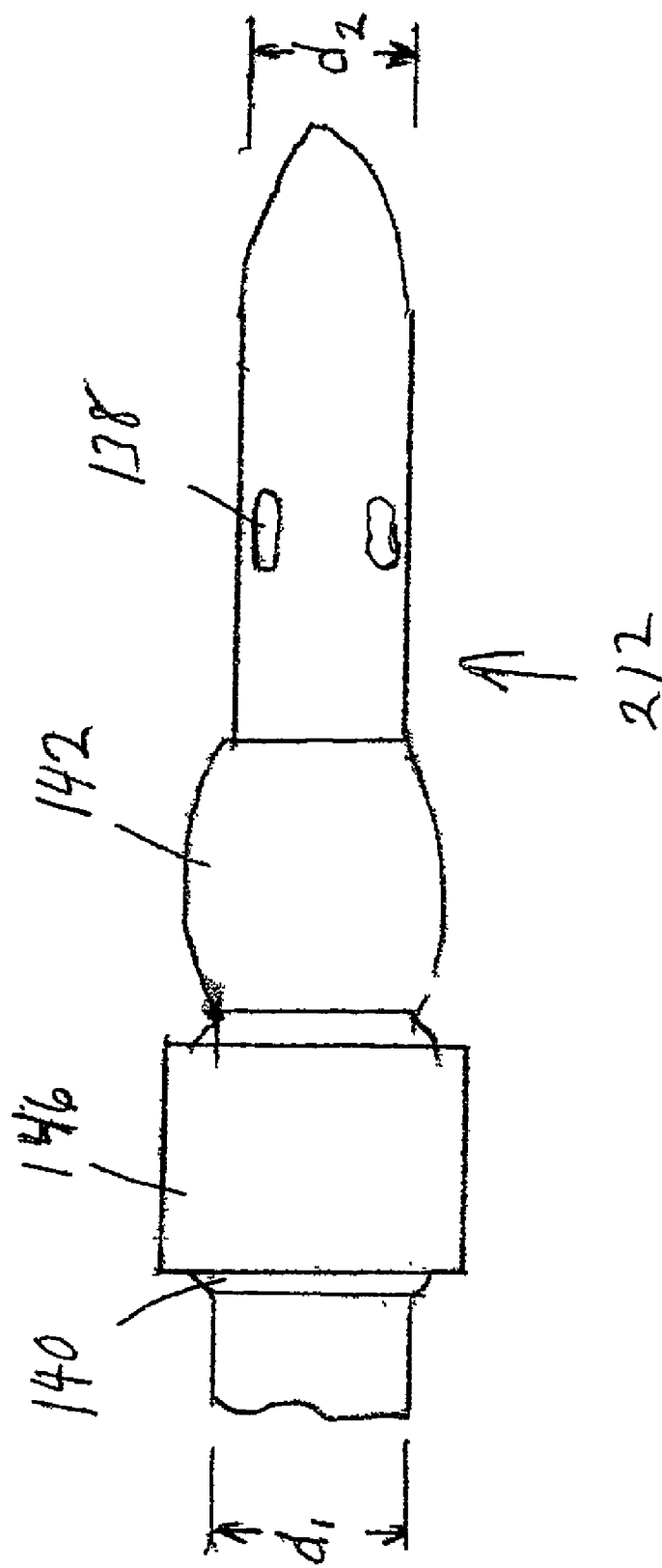
FIG. 8 is a side elevational view of a third embodiment of a catheter system according to the invention.

A third embodiment of the invention is illustrated in FIG. 8. This embodiment differs from those previously described in two basic respects: balloons 140 and 142 are mounted directly adjacent to one another; and the outer diameter of catheter 212 changes along the length of the catheter, having a larger value, $d_1$, at least in the region aligned with balloon 140 and a smaller diameter, $d_2$, over all or a part of its length between balloon 140 and the distal end of the catheter. This configuration will act as a sump that increase blood flow through lumen 122. In addition, as described above with respect the embodiment of FIGS. 4–7, the wall thickness of catheter 212 in the region between balloon 140 and the distal end can be smaller than in the region aligned with balloon 140. In practical embodiments of the catheter of FIG. 8, $d_1$ can have a value between 3 and 5 Fr and $d_2$ can have a value between 2 and 4 Fr, with $d_1$ always being greater than $d_2$.

By placing balloon 142 directly adjacent balloon 140, it becomes possible to better prevent the escape of debris at locations that are directly adjacent to a side branch of the artery being treated. Balloon 140 and 142 can be mounted so that their facing edges abut one another.

According to other possibilities, the catheter system can be constructed so that balloons 140 and 142 are movable longitudinally relatively to one another, for example as disclosed in issued U.S. Pat. No. 5,342,306. According to another possibility, balloon 142 can be spaced from balloon 140 and can be constructed in a manner to expand parallel to the axis of the catheter in a direction toward balloon 140, as disclosed in U.S. Pat. No. 5,380,284. The contents of these patents are incorporated herein by reference. Both of these alternatives allow the practitioner to better deal with situations in which the region on which an angioplasty treatment is to be performed is located directly adjacent a side branch of the artery being treated.

Embodiments of the invention can possess one or both of the features described above with reference to FIG. 8

Figure 2:
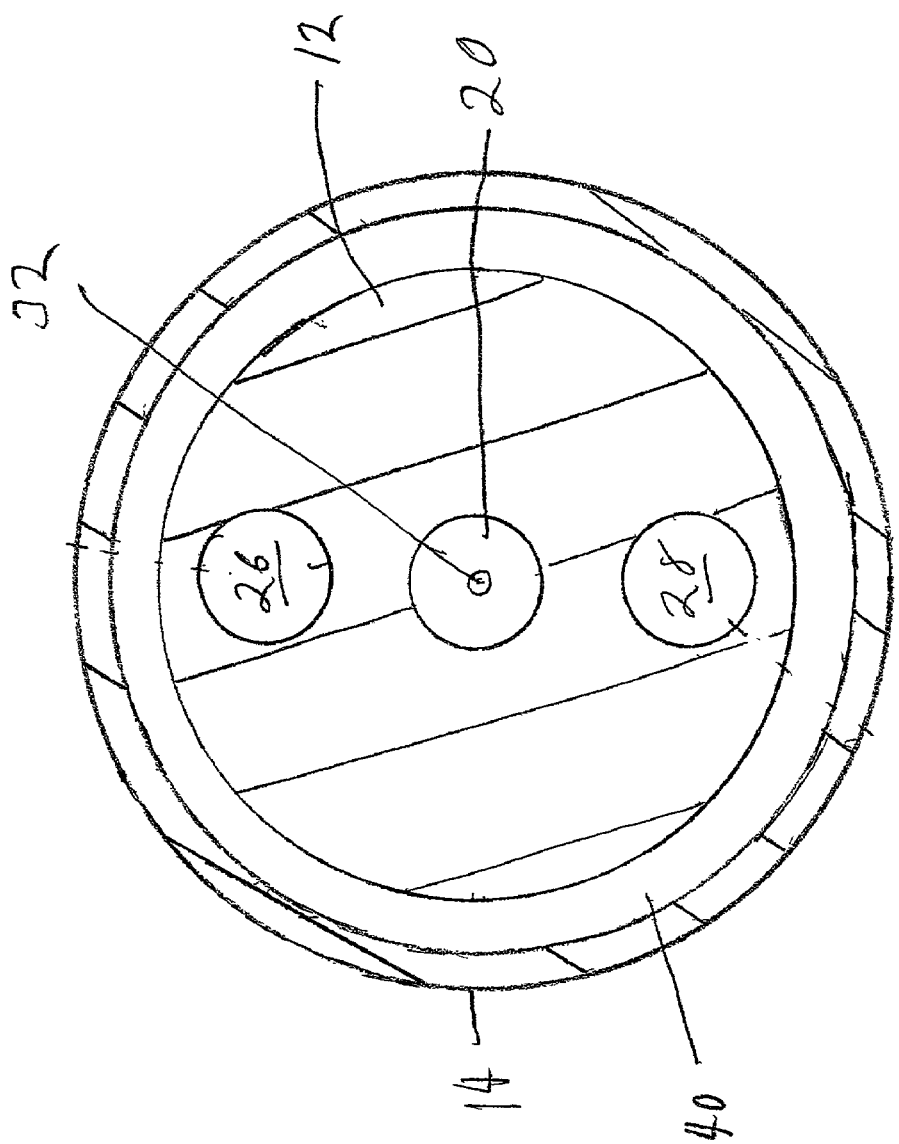
FIGS. 2 and 3 are cross-sectional views taken along lines 2—2 and 3—3, respectively, of FIG. 1.

The above-described device is manipulated to perform an angioplasty treatment in the same manner as described earlier herein with respect to the embodiment shown in FIGS. 1–3.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A system for performing a medical treatment in a blood vessel while providing downstream microcirculatory system protection, said system comprising:

a catheter having a longitudinal axis, a distal end, an outer lateral surface, a central blood bypass flow lumen extending along the longitudinal axis and opening at said distal end, blood flow inlet and outlet openings extending from said lateral surface and communicating with said bypass flow lumen, and first and second inflation lumens extending to said lateral surface at respective first and second locations that are spaced apart along the longitudinal axis and that are between said inlet openings and said outlet openings; and first and second inflatable members secured to said lateral surface and each having an interior that communicates with only a respective one of said first and second inflation lumens, wherein said catheter has a thin outer wall with a thickness of about 0.127 mm, enclosing a hollow interior that is completely occupied by said bypass flow lumen, except for the space occupied by said first and second inflation lumens.

2. The system of claim 1 further comprising: a tube dimensioned to surround, and to be movable parallel to the longitudinal axis of, said catheter, and to move past at least one of said inflatable members when that inflatable member is deflated; and a suction source communicating with the interior of said tube.

3. The system of claim 2 wherein said catheter is tapered at said distal end.

4. The system of claim 2 further comprising an expandable stent mounted or crimped on said first inflatable member.

5. The system of claim 2 wherein said first inflatable member is a low compliance angioplasty balloon, or sheath, or sleeve, and said second inflatable member is a high compliance blocking balloon and is located between said first inflatable member said outlet openings.

6. The system of claim 5 wherein said catheter has an outer diameter with a first value in a first region aligned with said first inflatable member and a second value smaller than the first value in a second region located between said first region and said distal end.

7. The system of claim 5 wherein said thin outer wall of said catheter has a first thickness value in a first region aligned with said first inflatable member and a second thickness value smaller than the first thickness value in a second region located between said first region and said distal end.

8. The system of claim 2 wherein there are a plurality of said inlet openings distributed around the longitudinal axis, and a plurality of said outlet openings distributed around the longitudinal axis, and said outlet openings are located between said inlet openings and said distal end.

9. The system of claim 1 wherein said catheter is tapered at said distal end.

10. The system of claim 1 wherein said first inflatable member is a low compliance angioplasty balloon, or sheath, or sleeve, and said second inflatable member is a high compliance blocking balloon and is located between said first inflatable member said outlet openings.

11. The system of claim 1 wherein there are a plurality of said inlet openings distributed around the longitudinal axis, and a plurality of said outlet openings distributed around the longitudinal axis, and said outlet openings are located between said inlet openings and said distal end.

12. The system of claim 1 further comprising an expandable stent mounted or crimped on said first inflatable member.

13. The system of claim 1 wherein said first and second inflatable members are directly adjacent one another.

14. The system of claim 13 wherein said first and second inflatable members abut against one another.

15. The system of claim 1 wherein said first and second inflation lumens are spaced from one another about said longitudinal axis of said catheter.

16. A system for performing a medical treatment in a blood vessel while providing downstream microcirculatory system protection, said system comprising:

a catheter having a longitudinal axis, a distal end, an outer lateral surface, a central blood bypass flow lumen extending along the longitudinal axis and opening at said distal end, blood flow inlet and outlet openings extending from said lateral surface and communicating with said bypass flow lumen, and first and second inflation lumens extending to said lateral surface at respective first and second locations that are spaced apart along the longitudinal axis and that are between said inlet openings and said outlet openings; and first and second inflatable members secured to said lateral surface and each having an interior that communicates with only a respective one of said first and second inflation lumens, wherein said catheter has a thin outer wall enclosing a hollow interior that is completely occupied by said bypass flow lumen, except for the space occupied by said first and second inflation lumens, said catheter is tapered at said distal end, and said catheter has an outer diameter with a first value in a first region aligned with said first inflatable member and a second value smaller than the first value in a second region located between said first region and said distal end.

17. A system for performing a medical treatment in a blood vessel while providing downstream microcirculatory system protection, said system comprising:

a catheter having a longitudinal axis, a distal end, an outer lateral surface, a central blood bypass flow lumen extending along the longitudinal axis and opening at said distal end, blood flow inlet and outlet openings extending from said lateral surface and communicating with said bypass flow lumen, and first and second inflation lumens extending to said lateral surface at respective first and second locations that are spaced apart along the longitudinal axis and that are between said inlet openings and sail outlet openings; and first and second inflatable members secured to said lateral surface and each having an interior that communicates with only a respective one of said first and second inflation lumens, wherein said catheter has a thin outer wall enclosing a hollow interior that is completely occupied by said bypass flow lumen, except for the space occupied by said first and second inflation lumens, said catheter is tapered at said distal end, and said thin outer wall of said catheter has a first thickness value in a first region aligned with said first inflatable member and a second thickness value smaller than the first thickness value in a second region located between said first region and said distal end.

* * * * *